United States Patent
Shimizu et al.

(10) Patent No.: US 10,407,380 B2
(45) Date of Patent: Sep. 10, 2019

(54) ISOMERIZATION METHOD FOR CYCLOHEXANEDIAMINE

(71) Applicant: Mitsubishi Gas Chemical Company, Inc., Chiyoda-ku (JP)

(72) Inventors: Yuko Shimizu, Chiyoda-ku (JP); Yoshiaki Yamamoto, Katsushika-ku (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 17 days.

(21) Appl. No.: 15/556,416

(22) PCT Filed: Feb. 25, 2016

(86) PCT No.: PCT/JP2016/055609
§ 371 (c)(1),
(2) Date: Sep. 7, 2017

(87) PCT Pub. No.: WO2016/143536
PCT Pub. Date: Sep. 15, 2016

(65) Prior Publication Data
US 2018/0037536 A1 Feb. 8, 2018

(30) Foreign Application Priority Data
Mar. 9, 2015 (JP) ................................. 2015-045793

(51) Int. Cl.
*C07B 61/00* (2006.01)
*C07C 209/68* (2006.01)
*C07C 211/36* (2006.01)

(52) U.S. Cl.
CPC .......... *C07C 209/68* (2013.01); *C07C 211/36* (2013.01); *C07B 61/00* (2013.01); *C07C 2601/14* (2017.05)

(58) Field of Classification Search
CPC ............................ C07C 209/68; C07C 211/36; C07C 2601/14; C07B 61/00
See application file for complete search history.

(56) References Cited

U.S. PATENT DOCUMENTS

| | | | | |
|---|---|---|---|---|
| 3,344,164 A | * | 9/1967 | Seaton .................. | C07C 211/18 558/356 |
| 3,499,925 A | * | 3/1970 | Inaoka ................. | A61K 31/195 562/507 |
| 3,657,345 A | | 4/1972 | Brake | |
| 4,026,943 A | | 5/1977 | Richter | |
| 4,086,276 A | * | 4/1978 | Butte, Jr. ............... | C07C 211/18 564/444 |
| 5,969,187 A | * | 10/1999 | Okawa .................. | C07C 209/68 564/444 |
| 2016/0207877 A1 | | 7/2016 | Yamamoto et al. | |

FOREIGN PATENT DOCUMENTS

| | | |
|---|---|---|
| CA | 2117928 A1 | 4/1995 |
| CN | 105555754 B | 10/2017 |
| JP | 7-188128 A | 7/1995 |
| JP | 2008-74754 A | 4/2008 |
| JP | 2015-13833 A | 1/2015 |
| SU | 41871 | 3/1974 |
| WO | 2015/041262 A1 | 3/2015 |

OTHER PUBLICATIONS

International Search Report dated May 24, 2016, in PCT/JP2016/055609, filed Feb. 25, 2016.

* cited by examiner

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

The present invention provides a method for isomerizing a cyclohexanediamine, which simply and highly actively realizes an isomerization reaction of a cyclohexanediamine, without passing through a high-pressure reaction and a complicated multi-stage process. The isomerization method has an isomerization step of isomerizing a cyclohexanediamine in the presence of a compound represented by the following formula (1) and at least one selected from the group consisting of an alkali metal, an alkali metal-containing compound, an alkaline earth metal or an alkaline earth metal-containing compound.

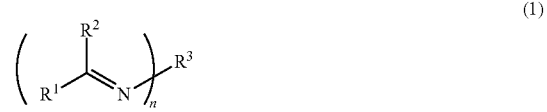

(1)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring); $R^3$ represents a hydrogen atom and an n-valent group selected from the group consisting of a substituted or unsubstituted hydrocarbon group; and n represents, an integer of 1 to 10.

11 Claims, 1 Drawing Sheet

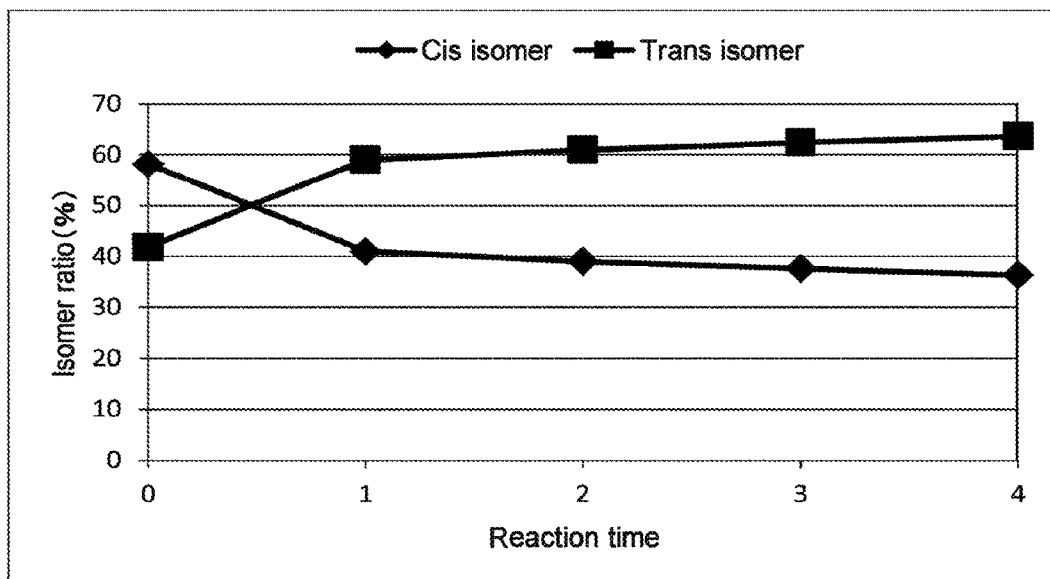

ISOMERIZATION METHOD FOR CYCLOHEXANEDIAMINE

TECHNICAL FIELD

The present invention relates to an isomerization method for cyclohexanediamine.

BACKGROUND ART

Cyclohexanediamine is an industrially important compound to be used as a raw material for e.g., epoxy curing agents and polyurethanes. A cyclohexanediamine has two isomers, i.e., a cis isomer and a trans isomer, derived from the cyclohexane ring.

Trans-1,4-bis(isocyanatocyclohexane) obtained from a trans isomer of 1,4-cyclohexanediamine is particularly useful as a polyurethane material and a cis isomer of 1,4-cyclohexanediamine, which can liquefy, is particularly useful as a curing agent for epoxy resins.

For these reasons, it is extremely important to control the isomer ratio of a cyclohexanediamine. As a method for controlling the isomer ratio of a cyclohexanediamine, various methods have been proposed.

As a method for controlling an isomer ratio, for example, a method of isomerizing 1,4-cyclohexanediamine in the presence of a noble metal catalyst under high temperature and high pressure conditions is known (Patent Literature 1, Patent Literature 2).

Another method is disclosed, in which p-phenylenediamine is nuclear-hydrogenated; and from the resultant mixture of a cis isomer and trans isomer of 1,4-cyclohexanediamine, the trans isomer is separated by e.g., crystallization; and the filtrate rich in the cis isomer is fed back (for recycling) to an isomerization step (Patent Literature 1, Patent Literature 3).

CITATION LIST

Patent Documents

Patent Document 1: U.S. Pat. No. 3,657,345
Patent Document 2: Japanese Patent Application Laid-open No. 2015-13833
Patent Document 3: Japanese Patent Application Laid-Open No. 2008-74754

SUMMARY OF INVENTION

Technical Problem

However, the methods described in Patent Literatures 1 and 2, which employ an expensive, noble metal catalyst and high-pressure conditions, are industrially not easily carried out. Furthermore, even in the methods described in Patent Literatures 1 and 3, isomerization of a cis isomer must be carried out under high pressure conditions.

In the circumstances, it has been desired to develop a method for easily carrying out the isomerization reaction of a cyclohexanediamine.

The present invention was attained in consideration of the aforementioned problems. An object of the present invention is to provide a method for simply and highly actively realizing an isomerization reaction of an industrially important compound, i.e., cyclohexanediamine, without passing through a high-pressure reaction and a complicated multi-stage process.

Solution to Problem

The present inventors intensively conducted studies with a view to solving the aforementioned problems. As a result, they found that the above problems can be solved by an isomerization method having a predetermined isomerization step and arrived at the present invention.

More specifically, the present invention is as follows.

[1] A method for isomerizing a cyclohexanediamine, comprising a step of: isomerizing the cyclohexanediamine in a presence of an imine compound represented by following general formula (1) and at least one selected from the group consisting of an alkali metal, an alkali metal-containing compound, an alkaline earth metal and an alkaline earth metal-containing compound.

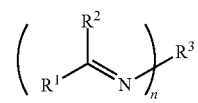

(1)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring); $R^3$ represents a hydrogen atom or an n-valent group selected from the group consisting of a substituted or unsubstituted hydrocarbon group; and n represents an integer of 1 to 10.

[2] The method for isomerizing a cyclohexanediamine according to [1], wherein the substituted or unsubstituted hydrocarbon group represented by each of $R^1$ and $R^2$ comprises a monovalent group selected from the group consisting of a substituted or unsubstituted aliphatic hydrocarbon group, a substituted or unsubstituted alicyclic hydrocarbon group and a substituted or unsubstituted aromatic hydrocarbon group; and the substituted or unsubstituted hydrocarbon group represented by comprises an n-valent group selected from the group consisting of a substituted or unsubstituted aliphatic hydrocarbon group, a substituted or unsubstituted alicyclic hydrocarbon group and a substituted for unsubstituted aromatic hydrocarbon group.

[3] The method for isomerizing a cyclohexanediamine according to [1] or [2], wherein the imine compound comprises a compound represented by following general formula (2) and/or a compound represented by following general formula (3):

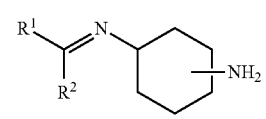

(2)

where in $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring);

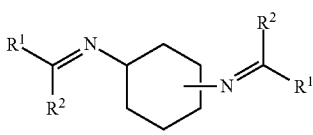

(3)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring).

[4] The method for isomerizing a cyclohexanediamine according to any one of [1] to [3], wherein the imine compound comprises a compound represented by following general formula (2a) and/or a compound represented by following general formula (3a).

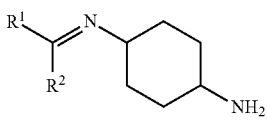

(2a)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring).

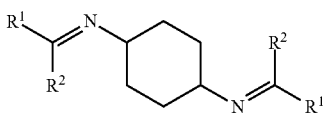

(3a)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring).

[5] The method for isomerizing a cyclohexanediamine according to any one of [1] to [4], wherein the imine compound is obtained by dehydration condensation between a primary amine and an aldehyde and/or a ketone.

[6] The method for isomerizing a cyclohexanediamine according to any one of [1] to [5], wherein the imine compound is obtained by dehydration condensation between the cyclohexanediamine and an aldehyde and/or a ketone.

[7] The method for isomerizing a cyclohexanediamine according to any one of [1] to [6], wherein the cyclohexanediamine is 1,4-cyclohexanediamine.

[8] The method for isomerizing a cyclohexanediamine according to any one of [1] to [7], wherein the alkali metal-containing compound comprises at least one selected from the group consisting of an alkali metal hydride and an alkali metal amide.

[9] The method for isomerizing a cyclohexanediamine according to any one of [1] to [8], wherein an isomerization reaction temperature in the step of isomerizing is 100 to 140° C.

[10] The method for isomerizing a cyclohexanediamine according to [9], wherein, in the step of isomerizing, a solvent having a boiling point equal to or lower than the isomerization reaction temperature is used.

[11] The method for isomerizing a cyclohexanediamine according to any one of [1] to [10], wherein, in the step of isomerizing, bubbling is performed by an inert gas.

Advantageous Effects of Invention

According to this invention, it is possible to provide a method for isomerizing a cyclohexanediamine, which simply and highly actively realize an isomerization reaction of an industrially important compound, i.e., cyclohexanediamine, without passing through a high-pressure reaction and a complicated multi-stage process, compared to techniques known in the art.

BRIEF DESCRIPTION OF DRAWINGS

The FIGURE shows a change in isomer ratio with the passage of time in Example 1.

DESCRIPTION OF EMBODIMENTS

Now, embodiments (hereinafter referred to as "the present embodiment") for carrying out the invention will be more specifically described below; however, the present invention is not limited to this and can be modified without departing from the scope of the invention.

[Method for Isomerizing a Cyclohexanediamine]

The isomerization method of a cyclohexanediamine according to the present embodiment has an isomerization step of isomerizing a cyclohexanediamine in the presence of an imine compound represented by the following general formula (1) and at least one selected from the group consisting of an alkali metal, an alkali metal-containing compound, an alkaline earth metal and an alkaline earth metal-containing compound (hereinafter collectively referred to as an "alkali metal (s)").

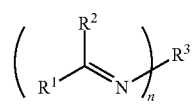

(1)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring); $R^3$ represents a hydrogen atom or an n-valent group selected from the group consisting of a substituted or unsubstituted hydrocarbon group; and n represents an integer of 1 to 10.

In the isomerization method of a cyclohexanediamine according to the present embodiment, with the above constitution, an active species of an isomerization catalyst can be produced in the step of isomerizing. Owing to this, an isomerization reaction of a cyclohexanediamine can be simply and highly actively carried out without passing through a high-pressure reaction and a complicated multi-stage process, compared to techniques known in the art.

[Isomerization Step]

The step of isomerizing is a step of isomerizing a cyclohexanediamine in the presence of an imine compound represented by the above general formula (1) and at least one selected from the group consisting of an alkali metal, an alkali metal-containing compound, an alkaline earth metal and an alkaline earth metal-containing compound.

The "isomerizing" refers to converting a trans isomer of a cyclohexanediamine to a cis isomer thereof or converting a cis isomer of a cyclohexanediamine to a trans isomer thereof.

The isomerization reaction temperature in the step of isomerizing is preferably 10 to 200° C., more preferably 80 to 150° C. and further preferably 100 to 140° C. If the isomerization reaction temperature is 10° C. or more, an isomerization reaction tends to be able to more efficiently proceed. If the isomerization reaction temperature is 200° C. or less, a side reaction, such as a decomposition react ion and a polymerization reaction can be suppressed and co-production of low-boiling point products and high-boiling point products can be reduced, with the result that the recovery rate of cyclohexanediamine tends to be more improved. Particularly, if the isomerization reaction temperature is controlled to be 100 to 140° C., a good yield and reaction rate tend to be successfully obtained.

The isomerization reaction time varies depending upon e.g., the use amounts of individual components, reaction conditions and the desired isomer composition; however, the reaction time is preferably 0.50 to 6.0 hours and more preferably 1.0 to 5.0 hours.

The isomerization reaction can be carried out either in the presence or absence of a solvent. As the solvent that can be used, although it is not particularly limited, for example, a solvent inert to a primary amine, an aldehyde and a ketone, are mentioned. Examples of such a solvent include, but are not particularly limited to, aromatic-based solvents such as benzene, toluene or xylene; ether solvents such as diethyl ether or tetrahydrofuran; and hydrocarbon-based solvents such as hexane or heptane. Of them, in order to more effectively promote the isomerization reaction, a solvent having a boiling point equal to or lower than an isomerization reaction temperature is preferable.

As the isomerization reaction atmosphere, although it is not particularly limited, for example, an atmosphere not containing air or active hydrogen such as water or an alcohol, is preferable. If such an atmosphere is employed, an active species of an isomerization catalyst, which is produced by adding an imine compound represented by formula (1) and at least one selected from, the group consisting of the alkali metals, is rarely inactivated and the reaction efficiency tends to be more improved. Particularly, in order to suppress inactivation by the reaction of the active species of a catalyst with water possibly present in the reaction system, the water content in the reaction system is preferably controlled to be 1000 ppm or less. As a convenient method for preventing contamination with e.g., moisture and air, an isomerization reaction is preferably carried out in an atmosphere of an inert gas such as nitrogen, gas and argon gas.

In the step of isomerizing, bubbling is preferably performed by supplying an inert gas in the reaction system. If so, an isomerization reaction tends to be more effectively promoted.

[Cyclohexanediamine]

Examples of the cyclohexanediamine include, but are not particularly limited to, 1,2-cyclohexanediamine, 1,3-cyclohexanediamine and 1,4-cyclohexanediamine. Of them, 1,4-cyclohexanediamine is preferable since it more effectively exerts the effect of the present invention without fail. According to the method of the present embodiment, any one of the cyclohexane diamines can be isomerized. The cyclohexane diamines mentioned above can be used alone or in combination of two or more.

[Imine Compound]

The imine compound is a compound represented by the above general formula (1). The imine compound is used for forming an active species of an isomerization catalyst for a cyclohexanediamine. In the above general formula (1), $R^1$ and $R^2$ each independently represent a hydrogen atom, or a monovalent group selected from the group consisting of a substituted or unsubstituted hydrocarbon group, a substituted or unsubstituted alkoxy group and an acyl group ($R^1$ and $R^2$ may mutually bind to form a ring). Imine compounds may be used alone or in combination of two or more.

Examples of the substituted or unsubstituted hydrocarbon group represented by each of $R^1$ and $R^2$, include, but are not particularly limited to, a monovalent group selected from the group consisting of an alkyl group, an alkenyl group, an alkynyl group or a substituted or unsubstituted aliphatic hydrocarbon group obtained by substituting one or two or more hydrogen atoms thereof with substituent(s); a cycloalkyl group or a substituted or unsubstituted alicyclic hydrocarbon group obtained by substituting one or two or more hydrogen atoms thereof with substituent (s); and an alkylaryl group, arylalkyl group or a substituted or unsubstituted aromatic hydrocarbon group obtained by substituting one or two or more hydrogen atoms thereof with substituent(s). The aliphatic hydrocarbon groups may be linear or branched.

Examples of the linear aliphatic hydrocarbon group represented by each of $R^1$ and $R^2$ include, but are not particularly limited to, a methyl group, an ethyl group, a propyl group, a butyl group, a pentyl group, a hexyl group, a heptyl group, an octyl group and a decyl group. The linear aliphatic hydrocarbon group may be a linear aliphatic hydrocarbon group obtained by replacing a single bond that the linear aliphatic hydrocarbon group has with a double bond and/or a triple bond.

Examples of the branched aliphatic hydrocarbon group represented by $R^1$ and $R^2$ include, but are not particularly limited to, an isopropyl group, an isobutyl group, a sec-butyl group, a t-butyl group, an isopentyl group, a neopentyl group, a 2-hexyl group, a 2-octyl group and a 2-decyl group. The branched aliphatic hydrocarbon group may be a branched aliphatic hydrocarbon group obtained by replacing a single bond that the aliphatic hydrocarbon group has with a double bond and/or a triple bond.

Examples of the alicyclic hydrocarbon group represented by each of $R^1$ and $R^2$ include, but are not particularly limited to, a cyclopropyl group, a cyclobutyl group, a cyclohexyl group, a cyclopentyl group, a cyclooctyl group and a cyclodecyl group. The alicyclic hydrocarbon group may be an alicyclic hydrocarbon group obtained by replacing a single bond that the alicyclic hydrocarbon group has with a double bond and/or a triple bond. Particularly, as the alicyclic hydrocarbon group, an alicyclic hydrocarbon group having an amino group is preferable.

Examples of the aromatic hydrocarbon group represented by each of $R^1$ and $R^2$ include, but are not particularly limited to, a phenyl group, a naphthyl group, a benzyl group, a methylphenyl group, an ethylphenyl group, a methylnaphthyl group and a dimethylnaphthyl group. Of them, the aromatic hydrocarbon group is preferably a monovalent group selected from the group consisting of a substituted or unsubstituted benzyl group, a substituted or unsubstituted benzyl group, a substituted or unsubstituted monovalent phenyl group and a substituted or unsubstituted monovalent naphthyl group.

Examples of the substituted or unsubstituted phenyl group include, but are not particularly limited to, groups represented by the following general formula (4). Examples of the substituted or unsubstituted monovalent naphthyl group include, but are not particularly limited to, groups represented by the following general formula (5).

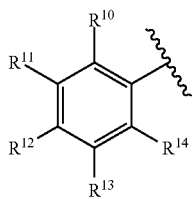

(4)

wherein $R^{10}$, $R^{11}$, $R^{12}$, $R^{13}$ and $R^{14}$ each independently represent a hydrogen atom, an alkyl group, having 1 to 10 carbon atoms, an alkoxy group having 1 to 10 carbon atoms, a phenyl group or an amino group.

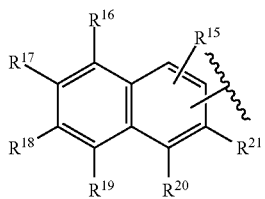

(5)

wherein $R^{15}$, $R^{16}$, $R^{17}$, $R^{18}$, $R^{19}$, $R^{20}$ and $R^{21}$ each independently represent a hydrogen atom, an alkyl group having 1 to 10 carbon atoms, an alkoxy group having 1 to 10 carbon atoms, a phenyl group or an amino group.

The number of carbon atoms of the substituted or unsubstituted hydrocarbon group represented by each of $R^1$ and $R^2$ is preferably 1 to 20, more preferably 1 to 12 and further preferably 1 to 10.

Examples of the substituted or unsubstituted alkoxy group represented by each of $R^1$ and $R^2$ include, but are not particularly limited to, a methoxy group, an ethoxy group, a propoxy group, a butoxy group, a pentyloxy group, a hexyloxy group, an octyloxy group and a decyloxy group. The alkoxy group may be an alkoxy group obtained by replacing a single bond that the alkoxy group has with a double bond and/or a triple bond.

The number of carbon atoms of the substituted or unsubstituted alkoxy group represented by each of $R^3$ and $R^2$ is preferably 1 to 10.

Examples of the substituted or unsubstituted aryloxy group represented by each of $R^1$ and $R^2$ include, but are not particularly limited to, a benzoyloxy group and a naphthyloxy group.

The number of carbon atoms of the substituted or unsubstituted aryloxy group represented by each of $R^1$ and $R^2$ is preferably 6 to 20, more preferably 6 to 12 and further preferably 6 to 10.

Examples of the substituents of the hydrocarbon group and alkoxy group represented by each of $R^1$ and $R^2$ include, but are not particularly limited to, an alkyl group, a carbonyl group, an amino group, an imino group, a cyano group, an azo group, an azide group, a nitro group, an acyl group, an aldehyde group, a cycloalkyl group and an aryl group.

Examples of the acyl group represented by each of $R^1$ and $R^2$ include, but are not particularly limited to, a formyl group, an acetyl group, a propanoyl group, a butanoyl group, a pentanoyl group, a hexanoyl group, an octanoyl group, and a benzoyl group. The hydrogen atom of the acyl group may be substituted with a substituent.

The number of carbon atoms of the acyl group represented by each of $R^1$ and $R^2$ is preferably 1 to 10.

Examples of the case where $R^1$ and $R^2$ mutually bind to form a ring, include, but are not particularly limited to, a case where $R^1$ and $R^2$ mutually bind to form an aliphatic ring and a case where $R^1$ and $R^2$ mutually bind to form a heterocyclic ring.

$R^3$ represents a hydrogen atom and an n-valent group selected from, the group consisting of a substituted or unsubstituted hydrocarbon group. Reference symbol n is an integer of 1 to 20, preferably 1 to 12, more preferably 1 to 10, further preferably 1 to 8, still further preferably 1 to 6, particularly preferably 1 to 4, and most preferably 1 to 2.

The substituted or unsubstituted hydrocarbon group represented by $R^3$, although it is not particularly limited, is, for example, an n-valent group selected from the group consisting of an alkyl group, an alkenyl group, an alkynyl group or a substituted or unsubstituted aliphatic hydrocarbon group obtained by substituting one or two or more hydrogen atoms thereof with a substituent(s) and an aliphatic hydrocarbon group obtained by removing n−1 hydrogen atoms from the above substituted or unsubstituted aliphatic hydrocarbon group; a cycloalkyl group or a substituted or unsubstituted alicyclic hydrocarbon group obtained by substituting one or two or more hydrogen atoms thereof with a substituent(s) and an alicyclic hydrocarbon group obtained by removing n−1 hydrogen atoms from the above substituted or unsubstituted alicyclic hydrocarbon group; and an alkylaryl group, an arylalkyl group, a benzyl group or a substituted or unsubstituted aromatic hydrocarbon group obtained by substituting one or two or more hydrogen atoms thereof with a substituent(s) and an aromatic hydrocarbon group obtained by removing n−1 hydrogen atoms front the above substituted or unsubstituted aromatic hydrocarbon group. The aliphatic hydrocarbon group may be linear or branched.

Examples of the linear aliphatic hydrocarbon group represented by $R^3$ include, but are not particularly limited to, a methyl group, an ethyl group, a propyl group, a butyl group, a pentyl group, a hexyl group, a heptyl group, an octyl group and a decyl group, and a group obtained by removing n−1 hydrogen atoms from, each of these groups. The linear aliphatic hydrocarbon group may be a linear aliphatic hydrocarbon group obtained by replacing a single bond that the aliphatic hydrocarbon group has with a double bond and/or a triple bond.

Examples of the branched aliphatic hydrocarbon group represented by $R^3$ include, but are not particularly limited to, an isopropyl group, an isobutyl group, a sec-butyl group, a t-butyl group, an isopentyl group, a neopentyl group, a 2-hexyl group, a 2-octyl group, and a 2-decyl group, and a group obtained by removing n−1 hydrogen atoms from each of these groups. The branched aliphatic hydrocarbon group may be a branched aliphatic hydrocarbon group obtained by replacing a single bond that the aliphatic hydrocarbon group has with a double bond and/or a triple bond.

Examples of the alicyclic hydrocarbon group represented by $R^3$ include, but are not particularly limited to, a cyclopropyl group, a cyclobutyl group, a cyclohexyl group, a cyclopentyl group, a cyclooctyl group, a cyclodecyl group and a cyclohexanedimethylene group, and a group obtained by removing n−1 hydrogen atoms from, each of these groups. The alicyclic hydrocarbon group may be an alicyclic hydrocarbon group obtained by replacing a single bond that the alicyclic hydrocarbon group has with a double bond and/or a triple bond. Particularly, the alicyclic hydrocarbon group is preferably an alicyclic hydrocarbon group having an amino group.

Examples of the aromatic hydrocarbon group represented by $R^3$ include, but are not particularly limited to, a phenyl group, a phenylene group, a naphthyl group, a naphthylene group, a benzyl group, a methylphenyl group, a methylphenylene group, an ethylphenyl group, an ethylphenylene group, a methylnaphthyl group, a methylnaphthylene group, a dimethyinaphthyl group, a dimethylnaphthylene group and a xylylene group, and a group obtained by removing n−1 hydrogen atoms from each of these groups.

The number of carbon atoms of the substituted or unsubstituted hydrocarbon group represented by $R^3$ is preferably 1 to 20, more preferably 1 to 12 and further preferably 1 to 10.

As the substituents of a hydrocarbon group represented by $R^3$, although it is not particularly limited, for example, the same substituents as defined in $R^1$ and $R^2$ are mentioned.

As the imine compound represented by the general formula (1), although it is not particularly limited, for example, a compound represented by the following general formula (2) and/or a compound represented by the following general formula (3) are preferable. If such a compound is used, production of by-products after isomerization can be suppressed and the amount of by-products to be separated can be decreased, with the result, that a highly purified cyclohexanediamine tends to be easily obtained. From, the same point of view, as the imine compound represented by the general formula (1), a compound represented by the following general formula (2a) and/or a compound represented by the following general formula (3a) are more preferable.

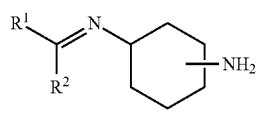

(2)

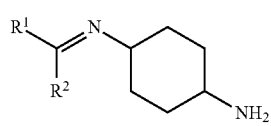

(2a)

wherein $R^1$ and $R^2$ each independently represent a hydrogen atom, or a monovalent group selected from the group consisting of a substituted or unsubstituted hydrocarbon group, a substituted or unsubstituted alkoxy group and an acyl group ($R^1$ and $R^2$ may mutually bind to form a ring).

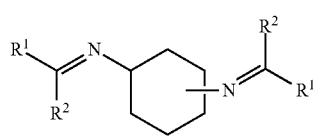

(3)

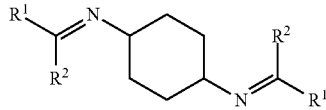

(3a)

wherein $R^1$ and $R^2$ each independently represent a hydrogen atom, or a monovalent group selected from the group consisting of a substituted or unsubstituted hydrocarbon group, a substituted or unsubstituted alkoxy group and an acyl group ($R^1$ and $R^2$ may mutually bind to form a ring).

In the above general formulas (2), (2a), (3) and (3a), $R^1$ and $R^2$ are the same as defined in the above general formula (1).

As the imine compound, not only a compound available as a reagent but also a compound obtained by organic synthesis can be used. Examples of the compound available as a reagent include, but are not particularly limited to, benzylidene aniline and N-benzylidene-tertiary butylamine. Examples of the compound obtained by organic synthesis include, but are not particularly limited to, imine compounds described in Chem. Rev., 1963, 63(5), pp 489-510 The CHEMISTRY OF IMINES, Table I to Table VII, which have a substituent containing a functional group inert to an alkali metal, an alkali metal amide, an alkali metal hydride, an alkaline earth metal or an alkaline earth metal hydride. These may be used without any purification.

The use amount of the imine compound, although it is not particularly limited, is preferably 0.001 to 0.10 mole, more preferably 0.005 to 0.05 moles relative to 1 mole of cyclohexanediamine. If the use amount of imine compound is 0.001 mole or more relative to 1 mole of cyclohexanediamine, the isomerization reaction tends to more quickly and smoothly proceed. In addition, if the use amount of the imine compound falls within the above range, a side reaction such as a polymerization reaction between cyclohexanediamine molecules can be suppressed, with the result that the yield of a desired isomer is more improved and catalyst cost tends to be successfully suppressed to a minimum. In the isomerization method of the present embodiment, if the use amount of the imine compound is the above catalyst amount, the reaction can efficiently proceed.

(Method for Synthesizing Imine Compound)

The imine compound is preferably obtained by dehydration condensation between a primary amine and an aldehyde and/or a ketone and more preferably dehydration condensation between a cyclohexanediamine and an aldehyde and/or a ketone. Such an imine compound may be added in the reaction system of the isomerization method of the present embodiment or may be produced in the reaction system.

Particularly, for isomerizing 1,4-cyclohexanediamine, an imine compound obtained by dehydration condensation between 1,4-cyclohexanediamine and an aldehyde or a ketone is more preferably used. If the imine compound obtained by the dehydration condensation reaction between 1,4-cyclohexanediamine and an aldehyde or a ketone is used, the amount of compounds to be separated decreases and the purity of 1,4-cyclohexanediamine becomes to be easily improved.

For isomerizing 1,3-cyclohexanediamine, an imine compound obtained by dehydration condensation between 1,3-cyclohexanediamine and an aldehyde or a ketone is more preferably used. If the imine compound obtained by the dehydration condensation reaction between 1,3-cyclohexanediamine and an aldehyde or a ketone is used, the amount of compounds to be separated decreases and the purity of 1,3-cyclohexanediamine is easily improved.

The above dehydration condensation reaction can be carried out in the presence or absence of a catalyst. The above dehydration condensation reaction can be also carried out in the presence or absence of a solvent. As the solvent that can be used herein, although it is not particularly limited, for example, solvents inert to a primary amine, an aldehyde and a ketone, are mentioned. Examples of the solvents include, but are not particularly limited to, aromatic-based solvents such as benzene, toluene or xylene; ether solvents such as diethyl ether or tetrahydrofuran; and hydrocarbon-based solvents such as hexane or heptane.

As a method for a dehydration condensation reaction, although it is not particularly limited, for example, specifically, an azeotropic dehydration method using a dean stark apparatus is mentioned. In this method, an imine compound can be easily obtained by azeotropically dehydrating each of the components in a benzene solvent. In the case where a dehydration condensation reaction is carried out in the absence of a solvent, the dehydration condensation can easily progress by removing water from the reaction system by e.g., a distillation operation.

In the case where an imine compound is prepared in an isomerization reaction system, the isomerization method of the present embodiment may have, before and/or after the step of isomerizing, a dehydration condensation step in which a cyclohexanediamine is mixed with an aldehyde and/or a ketone and subjected to a dehydration condensation, thereby obtaining an imine compound in the reaction system.

If the isomerization method has the dehydration condensation step, a cyclohexanediamine can be isomerized by adding an alkali metal in the reaction system without isolating an imine compound obtained through the dehydration condensation between an aldehyde or ketone and a primary amine.

If the isomerization method has the dehydration condensation step, an aldehyde or a ketone, which is industrially easily and inexpensively available, can be used as a raw material for a catalyst, without using e.g., an expensive noble metal. As a result, isomerization of a cyclohexanediamine can be industrially advantageously carried out. Thus, the dehydration condensation step has extremely high industrial significance.

(Primary Amine)

As the primary amine, although it is not particularly limited, for example, a compound generally available and providing an imine compound having a substituent containing a functional group inert to an alkali metal, etc., is mentioned. The primary amine may be used alone or in combination (of two or more); however, a single primary amine is preferably used alone, in order to simplify the industrial process.

Examples of the primary amine include, but are not particularly limited to, methylamine, ethylamine, propylamine, isopropylamine, butylamine, isobutylamine, tert-butylamine, benzylamine, methylbenzylamine, dimethylbenzylamine, aniline, meta-xylylenediamine, para-xylylenediamine, cyclohexylaminie, 1,3-bis(aminomethyl) cyclohexane or 1,4-bis(aminomethyl) cyclohexane, isophoronediamine, o-phenylenediamine, m-phenylenediamine, p-phenylenediamine, phenethylamine, diaminodiphenylmethane, methanediamine, ethanediamine, propanediamine, butanediamine, pentanediamine, hexanediamine, 1,4-cyclohexanediamine, 1,3-cyclohexanediamine and 1,2-cyclohexanediamine.

Of them, a cyclohexanediamine is preferable. If a cyclohexanediamine, which is a target compound to be isomerized, is used, an isomerization reaction can be carried out without using another amine and the resultant cyclohexanediamine tends to be more simply purified.

(Aldehyde)

As the aldehyde, although it is not particularly limited, for example, a compound generally available and having a substituent containing a functional group inert to an alkali metal, is mentioned. As such an aldehyde, although it is not particularly limited, for example, at least one selected from the group consisting of an aliphatic aldehyde represented by the following general formula (6), an aromatic aldehyde represented by the following general formula (7) and an aromatic aldehyde represented by the following general formula (8) is mentioned. If such a compound is used, an isomerization yield tends to be more improved.

(6)

wherein $R^{22}$ represents a hydrogen atom or a monovalent substituent selected from, the group consisting of a substituted or unsubstituted aliphatic hydrocarbon group and a substituted or unsubstituted alicyclic hydrocarbon group.

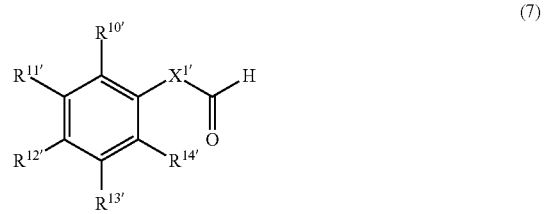

(7)

wherein $R^{10'}$, $R^{11'}$, $R^{12'}$, $R^{13'}$ and $R^{14'}$ each independently represent a hydrogen atom or a monovalent group selected from the group consisting of an alky group having 1 to 10 carbon atoms, an alkoxy group having 1 to 10 carbon atoms, a phenyl group and an amino group; and $X^{1'}$ represents a single bond or a divalent alkyl group having 1 to 10 carbon atoms.

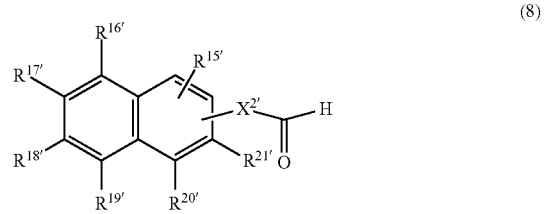

(8)

wherein $R^{15'}$, $R^{16'}$, $R^{17'}$, $R^{18'}$, $R^{19'}$, $R^{20'}$ and $R^{21'}$ each independently represent a hydrogen atom or a monovalent group selected from the group consisting of an alkyl group having 1 to 10 carbon atoms, an alkoxy group having 1 to 10 carbon atoms, a phenyl group and an amino group; and $X^{2'}$ represents a single bond or a divalent alkyl group having 1 to 10 carbon atoms.

As the above aldehyde, although it is not particularly limited, for example, formaldehyde, an aliphatic aldehyde and an aromatic aldehyde are mentioned. If such a compound is used, an isomerization yield tends to be more improved. Aldehydes may be used alone or in combination (of two or more); however, a single aldehyde, is preferably used alone in order to simplify the industrial process.

Examples of the aliphatic aldehyde include, but are not particularly limited to, acetaldehyde, propionaldehyde, 4-isopropylaldehyde, isobutyraldehyde, n-butyraldehyde, n-valeraldehyde, isovaleraldehyde, pivalaldehyde, n-hexylaldehyde, n-heptylaldehyde, n-octylaldehyde, n-nonylaldehyde, n-decylaldehyde, acrolein, methacrolein, 2-methylpentanal, crotonaldehyde, cinnamaldehyde, phenylacetaldehyde, p-methylphenylacetaldehyde, glyoxal, glutaraldehyde, hydroxypivalaldehyde, (+)-citronellal and (−)-citronellal. Of them, at least one selected from the group consisting of acetaldehyde, isobutyraldehyde, n-decylaldehyde, methacrolein, cinnamaldehyde and glyoxal, is preferable. If such a compound is used, an isomerization yield tends to be more improved.

Examples of the aromatic aldehyde include, but are not particularly limited to, benzaldehyde, 2-methylbenzaldehyde, 3-methylbenzaldehyde, 4-methylbenzaldehyde, 2-ethylbenzaldehyde, 3-ethylbenzaldehyde, 4-ethylbenzaldehyde, 2-propylbenzaldehyde 3-propylbenzaldehyde, 4-propylbenzaldehyde, 2-isopropylbenzaldehyde, 3-isopropylbenzaldehyde, 4-isopropylbenzaldehyde, 4-biphenylaldehyde, 2-butylbenzaldehyde, 3-butylbenzaldehyde, 4-butylbenzaldehyde, 2-tert-butylbenzaldehyde, 3 tertiary butylbenzaldehyde, 4-tertiary butylbenzaldehyde, 2-phenylbenzaldehyde, 3-phenylbenzaldehyde, 4-phenylbenzaldehyde, 2,3-dimethylbenzaldehyde, 2,4-dimethylbenzaldehyde, 2,5-dimethylbenzaldehyde, 2,6-dimethylbenzaldehyde, 3,4 dimethylbenzaldehyde, 3,5-dimethylbenzaldehyde, 2,4,5-trimethylbenzaldehyde, 2,4,6-trimethylbenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 1-naphthaldehyde, 2-naphthaldehyde and 3-naphthaldehyde. Of them, at least one compound selected from the group consisting of benzaldehyde, 4-methylbenzaldehyde, 4-ethylbenzaldehyde, 4-isopropylbenzaldehyde, 2,4-dimethylbenzaldehyde, 3,4-dimethylbenzaldehyde, 2,4,5-trimethylbenzaldehyde, 2,4,6-trimethylbenzaldehyde, 4-isobutylbenzaldehyde and 4-biphenylaldehyde, is preferable. If such a compound is used, an isomerization yield tends to be more improved.

The use amount of aldehyde is preferably 0.001 to 0.10 mole and more preferably 0.005 to 0.05 moles relative to 1 mole of cyclohexanediamine. If the use amount of the aldehyde fails within the above range, the isomerization reaction more quickly and smoothly proceeds and a side reaction such as a polymerization reaction between cyclohexanediamine molecules can be suppressed, with the result that the yield of a desired isomer is more improved and catalyst cost tends to be successfully suppressed to a minimum.

(Ketone)

As the ketone, although it is not particularly limited, for example, a compound generally available and providing a compound having a substituent containing a functional group inert to an alkali metal, is mentioned. As such a ketone, although it is not particularly limited, for example, at least one selected from the group consisting of an aliphatic ketone, an aromatic ketone, an aliphatic aromatic ketone and a cyclic ketone, is mentioned. If such a compound is used, the trans isomer ratio or cis isomer ratio of the obtained isomers and an isomerization yield tend to be more improved. Ketones may be used alone or in combination (of two or more); however, a single ketone is preferably used alone in order to simplify the industrial process.

Examples of the aliphatic ketone include, but are not particularly limited to, acetone, methyl ethyl ketone, diethyl ketone, methyl propyl ketone, methyl isobutyl ketone, ethyl propyl ketone, ethyl isobutyl ketone and dipropyl ketone.

Examples of the aromatic ketone include, but are not particularly limited to, benzophenone.

Examples of the aliphatic aromatic ketone include, but are not particularly limited to, acetophenone.

Examples of the cyclic ketone include, but are not particularly limited to, cyclohexanone.

Of them, at least one ketone selected from the group consisting of methyl ethyl ketone and acetophenone, is preferable. If such a compound is used, an isomerization yield tends to be more improved.

The use amount of the ketone is preferably 0.001 to 0.10 moles, more preferably 0.005 to 0.05 moles relative to 1 mole of cyclohexanediamine. If the use amount of the ketone falls within the above range, the isomerization reaction more quickly and smoothly proceeds and a side reaction such as a polymerization reaction between cyclohexanediamine molecules can be suppressed, with the result that the yield of a desired isomer is more improved and catalyst cost tends to be successfully suppressed to a minimum.

(Alkali Metals)

In the isomerization method of the present embodiment, a cyclohexanediamine is isomerized in the presence of at least one selected from the group consisting of an alkali metal, an alkali metal-containing compound, an alkaline-earth metal and alkaline-earth metal-containing compound. Owing to the presence of these alkali metals in the isomerization method of the present embodiment, an isomerization reaction can more quickly proceed. These alkali metals may be used alone or in combination of two or more.

Of the alkali metals, at least one selected from the group consisting of an alkali metal, an alkali metal hydride and an alkali metal amide is preferably contained; and at least one selected from the group consisting of metallic sodium, sodium amide and sodium hydride is more preferably contained. If such a substance is used, an isomerization yield tends to be more improve.

Examples of the alkali metals include, but are not particularly limited to, a metallic sodium, a metallic lithium and a metallic potassium.

Examples of the alkali metal-containing compounds include, but are not particularly limited to, an alkali metal hydride, an alkali metal amide, a basic oxide and an alkali metal alkoxide. If such a compound is used, the trans isomer ratio or cis isomer ratio of the obtained isomers and an isomerization yield tend to be more improved. Of them, at least one selected from the group consisting of an alkali metal hydride and an alkali metal amide, is preferable. Examples of the alkali metal hydride herein include, but are not particularly limited to, sodium hydride, lithium hydride, potassium hydride, lithium aluminum hydride and sodium boron hydride. Examples of the alkali metal amide include, but are not particularly limited to, sodium, amide, lithium amide, potassium amide, lithium diisopropylamide and sodium, bis(trimethylsilyl)amide. Examples of the basic oxide include, but are not particularly limited to, lithium oxide, sodium oxide, potassium oxide, cesium oxide, magnesium oxide, calcium oxide, strontium oxide and barium oxide. Examples of the alkali metal alkoxide include, but are not particularly limited to, potassium-tert-butoxide.

Examples of the alkaline-earth metal include, but are not particularly limited to, metallic magnesium and metallic calcium.

Examples of the alkaline-earth metal-containing compound include, but are not particularly limited to, an alkali earth metal hydride. Examples of the alkaline earth metal hydride include, but are not particularly limited to, calcium hydride and magnesium hydride.

The use amount of the compound as mentioned above, although it is not particularly limited, is preferably 0.001 to 0.10 mole and more preferably 0.005 to 0.05 moles relative to 1 mole of cyclohexanediamine. If the use amount of the compound as mentioned above fails within the above range, the isomerization reaction tends to more efficiently proceed.

The isomerization method of the present embodiment may have a purification step such as a catalyst component removal step of removing a catalyst component, a low boiling-point component removal step of removing low boiling-point components, a high boiling-point component removal step for removing high boiling-point components and an isomer separation step for distilling an isomer of a cyclohexanediamine. Note that the "catalytic component" herein more specifically refers to an imine compound and an alkali metal. The "low boiling-point components" refer to components having lower boiling points than those of isomers of a cyclohexanediamine. The "high boiling-point components" refer to components having higher boiling points than those of isomers of a cyclohexanediamine.

Note that the catalyst component removal step, low boiling-point component removal step, high boiling-point component removal step and isomer separation step may be carried out in a random order.

(Catalyst Component Removal Step)

The catalyst component removal step is a step of removing a catalytic component present in a react ion mixture after an isomerization step. Owing to the presence of the catalytic component removal step in the isomerization method of the present embodiment, a side reaction can be more suppressed from proceeding in the purification step. As the method of removing the catalyst, although it is not particularly limited, for example, thin-film distillation can be used. The catalytic component to be separated herein can be inactivated and then separated or can be separated in an active state. The catalytic component separated in an active state can be used again as a catalyst for an isomerization reaction.

(Low Boiling-Point Component Removal Step)

The low boiling-point component removal step is a step of removing low boiling-point components having lower boiling points than those of isomers of a cyclohexanediamine during or after an isomerization step. Owing to the presence of the low boiling-point component removal step in the isomerization method of the present embodiment, the yield of the isomer tends to be more improved. As the method of removing the low boiling-point components, although it is not particularly limited, for example, a method of performing distillation at a temperature equal to or lower than the boiling points of isomers of a cyclohexanediamine to remove low boiling-point components from the reaction mixture, is mentioned.

(High Boiling-Point Component Removal Step)

The high boiling-point component removal step is a step of removing high boiling-point components having higher boiling points than those of isomers of a cyclohexanediamine after an isomerization step. As the method of removing the high boiling-point components, although it is not particularly limited, for example, a method of distilling the isomers of a cyclohexanediamine from the reaction mixture in the following isomer separation step, and thereafter, removing high boiling-point components remaining in the reaction mixture, is mentioned.

(Isomer Separation Step)

The isomer separation step is a step of distilling a trans isomer and/or cis isomer of a cyclohexanediamine during and/or after the step of isomerizing. Owing to the presence of the isomer separation step in the isomerization method of the present embodiment, the yield of the isomer tends to be more improved.

As described above, the isomers of a cyclohexanediamine obtained by the method of the present embodiment can be isolated by a general method such as distillation. If distillation is carried out, isomerization is preferably carried out while separating isomerized cyclohexanediamine. In this manner, a cyclohexanediamine containing isomers in a high concentration which is equal to or higher than, that in the equivalent composition can be produced.

Note that distillation conditions such as distillation temperature can be appropriately controlled depending upon the desired isomer.

Now, a means for carrying out the isomerization method of the present embodiment will be described; however, the isomerization method of the present embodiment is not limited to the followings.

As the first aspect, the isomerization method of the present embodiment can be carried out by mixing an imine compound, an alkali metal and a cyclohexanediamine in a reactor. The reactor may have a heating means for heating the reactor, a stirring means for stirring the mixture in the reactor and a gas supply means for bubbling the mixture in the reactor.

To a reactor, an imine compound, an alkali metal, and a cyclohexanediamine may be added in a random manner. Two components are selected from an imine compound, an alkali metal and cyclohexanediamine and mixed in advance, and then, the mixture may be added. Alternatively, a mixture of an imine compound, an alkali metal or a cyclohexanediamine and a solvent may be added.

As an addition means for adding an imine compound, an alkali metal and a cyclohexanediamine, a means which can add these compounds at a time in a reactor or a means which can continuously add them dropwise may be employed.

The reactor may have a gas supply means and a gas exhaust means for controlling the atmosphere within the reactor. The reactor may be constituted so as to reflux a solvent. The reactor may be designed for a batch reaction or a continuous reaction.

As a second aspect, a first reactor for producing an imine compound by supplying a primary amine, an aldehyde and/or a ketone thereto and a second reactor for carrying out an isomerization reaction may be employed. In this case, the second reactor is designed to communicate with the first reactor such that the imine compound produced is supplied thereto. The first reactor and/or the second reactor may have a dehydration means (for example, a dean stark apparatus or a distillation apparatus) for removing water from the reaction system. Note that in the case where a cyclohexanediamine is used as the amine, the raw materials to be supplied to the second reactor may contain an imine compound and the cyclohexanediamine. Other structures can be the same as defined in the first aspect.

As a third aspect, a reactor for mixing an imine compound, an alkali metal and a cyclohexanediamine and a distiller communicating with the reactor may be employed.

17

In this case, the reactor and the distiller may be integrated into one body. Other structures can be the same as defined in the first aspect.

EXAMPLES

Now, the present invention will be more specifically described by way of Examples and Comparative Examples; however, the present invention is not limited to these Examples.

(Isomer Composition)

The isomer composition (cis/trans ratio) was analyzed by use of a gas chromatographic apparatus equipped with a capillary column, HP1-M, manufactured by Agilent. The trans isomer of 1,4-cyclohexanediamine had a lower boiling point than the cis isomer thereof. The isomer first detected by gas chromatography was a trans isomer and the isomer detected thereafter was a cis isomer. The ratio of the cis isomer was calculated in accordance with the formula:

Area value for cis isomer/(area value for cis isomer+
area value for trans isomer)×100.

The ratio of the trans isomer was calculated in accordance with the formula:

100−the ratio of the cis isomer.

(Isomerization Yield)

Isomerization yields were calculated by the internal standard method of the above gas chromatography analysis.

Isomerization yield(%)=(cyclohexanediamine after
the isomerization reaction)/(cyclohexanediamine
before isomerization reaction)×100

(Raw Materials)

4-Methyl-benzaldehyde, sodium amide and 1,4-cyclohexanediamine used herein were commercially available reagents.

Example 1

1,4-Cyclohexanediamine (cis isomer: 58.2%, trans isomer: 41.8%)(20.2 g) and 4-methyl-benzaldehyde (0.42 g) were weighed and placed in a 100-mL flask. The resultant mixture was stirred at 120° C. for 0.5 hours and thereafter dehydrated under reduced pressure (23 torr) at 120° C. After completion of dehydration, sodium amide (0.42 g) was added under an argon atmosphere and an isomerization reaction was carried out at normal pressure and 120° C. for 4 hours. Two hours after initiation of the reaction, the ratio of a cis isomer was 39.0%, the ratio of a trans isomer was 61.0%. Four hours after initiation of the reaction, the ratio of a cis isomer was 36.3%, the ratio of a trans isomer was 63.7%. The isomerization yield after four hours was 83.6%. The change in isomer ratio with the passage of time was shown in the FIGURE.

INDUSTRIAL APPLICABILITY

The cyclohexanediamine obtained by the isomerization method of the present invention has industrial applicability as optical materials to plastic lenses, prisms, optical fibers, information recording substrates, filters and the like using e.g., an epoxy resin and a polyurethane using a cyclohexanediamine.

18

The invention claimed is:

1. A method for isomerizing a cyclohexanediamine, comprising:
   isomerizing the cyclohexanediamine in the presence of an imine compound represented by formula (1) and
   at least one selected from the group consisting of an alkali metal, an alkali metal-containing compound, an alkaline earth metal and an alkaline earth metal-containing compound:

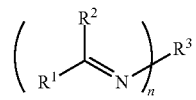

(1)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group, wherein $R^1$ and $R^2$ may mutually bond to form a ring; $R^3$ represents a hydrogen atom or an n-valent group selected from the group consisting of a substituted or unsubstituted hydrocarbon group; and n represents an integer of 1 to 10.

2. The method for isomerizing a cyclohexanediamine according to claim 1, wherein the substituted or unsubstituted hydrocarbon group represented by each of $R^1$ and $R^2$ comprises a monovalent group selected from the group consisting of a substituted or unsubstituted aliphatic hydrocarbon group, a substituted or unsubstituted alicyclic hydrocarbon group and a substituted or unsubstituted aromatic hydrocarbon group; and
   the substituted or unsubstituted hydrocarbon group represented by $R^3$ comprises an n-valent group selected from the group consisting of a substituted or unsubstituted aliphatic hydrocarbon group, a substituted or unsubstituted alicyclic hydrocarbon group and a substituted or unsubstituted aromatic hydrocarbon group.

3. The method for isomerizing a cyclohexanediamine according to claim 1, wherein the imine compound comprises a compound represented by formula (2) and/or a compound represented by formula (3):

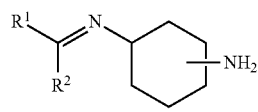

(2)

wherein in formula (2), $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group, wherein $R^1$ and $R^2$ may mutually bond to form a ring;

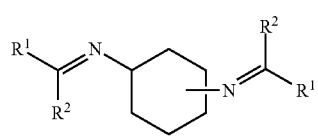

(3)

wherein in formula (3), $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group, wherein $R^1$ and $R^2$ may mutually bond to form a ring.

4. The method for isomerizing a cyclohexanediamine according to claim 1, wherein the imine compound comprises a compound represented by formula (2a) and/or a compound represented by formula (3a):

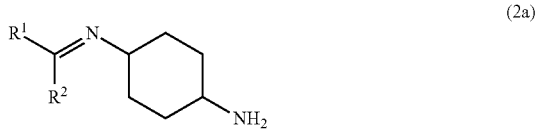

(2a)

wherein in formula (2a), $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group, wherein $R^1$ and $R^2$ may mutually bond to form a ring,

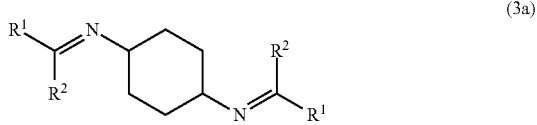

(3a)

wherein in formula (3a), $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group, wherein $R^1$ and $R^2$ may mutually bond to form a ring.

5. The method for isomerizing a cyclohexanediamine according to claim 1, wherein the imine compound is obtained by dehydration condensation between a primary amine and an aldehyde and/or a ketone.

6. The method for isomerizing a cyclohexanediamine according to claim 1, wherein the imine compound is obtained by dehydration condensation between the cyclohexanediamine and an aldehyde and/or a ketone.

7. The method for isomerizing a cyclohexanediamine according to claim 1, wherein the cyclohexanediamine is 1,4-cyclohexanediamine.

8. The method for isomerizing a cyclohexanediamine according to claim 1, wherein the alkali metal-containing compound comprises at least one selected from the group consisting of an alkali metal hydride and an alkali metal amide.

9. The method for isomerizing a cyclohexanediamine according to claim 1, wherein an isomerization reaction temperature in the isomerizing is 100 to 140° C.

10. The method for isomerizing a cyclohexanediamine according to claim 9, wherein, in the isomerizing, a solvent having a boiling point equal to or lower than the isomerization reaction temperature is used.

11. The method for isomerizing a cyclohexanediamine according to claim 1, wherein, in the isomerizing, bubbling is performed by an inert gas.

* * * * *